United States Patent [19]
Gadsby

[11] Patent Number: 5,830,367
[45] Date of Patent: Nov. 3, 1998

[54] METHOD OF USING INDICATOR MEANS FOR LIQUID PURIFICATION FILTER

[75] Inventor: Elizabeth Deibler Gadsby, Marietta, Ga.

[73] Assignee: Kimberly-Clark Worldwide, Inc., Neenan, Wis.

[21] Appl. No.: 764,676

[22] Filed: Dec. 11, 1996

[51] Int. Cl.$^6$ .......................... B01D 37/00; B01D 35/143; G01N 21/00
[52] U.S. Cl. .......................... 210/739; 210/745; 210/767; 356/436; 436/164
[58] Field of Search .................................. 210/85, 93, 94, 210/282, 739, 745, 767; 55/270, 274; 422/82.05; 436/164, 169, 172; 356/436

[56] References Cited

U.S. PATENT DOCUMENTS

| | | | |
|---|---|---|---|
| 3,664,095 | 5/1972 | Asker et al. | 55/387 |
| 5,110,479 | 5/1992 | Frommer et al. | 210/93 |
| 5,114,570 | 5/1992 | Nelson et al. | 210/94 |
| 5,494,744 | 2/1996 | Everhart et al. . | |

FOREIGN PATENT DOCUMENTS

| | | | |
|---|---|---|---|
| 59-189912 | 10/1984 | Japan | 210/85 |
| 64-56185 | 3/1989 | Japan | 210/85 |
| 95/33201 | 12/1995 | WIPO . | |

OTHER PUBLICATIONS

Derwent WPI Abstract for JP 03–284,349 dated Dec. 16, 1991.
Derwent WPI Abstract for SU 1,807,004 dated Apr. 7, 1993.

*Primary Examiner*—Joseph W. Drodge
*Attorney, Agent, or Firm*—William E. Maycock

[57] ABSTRACT

A method of monitoring the removal by a filter medium of a target substance from a liquid passing through the filter medium. The method involves: providing an indicator providing a filter medium having a plurality of binding sites which have a first affinity for the target substance and a second affinity for the indicator introducing the indicator means into the liquid; passing the liquid through the filter medium; and determining the presence or absence of the indicator in the liquid which has passed through the filter medium. The first and second affinities are adapted to require binding of the indicator by the filter medium only so long as binding sites are available to the target substance. Thus, the indicator means is adapted to compete with the target substance. As a practical matter, the liquid typically will be water. The indicator may denote when the filter medium is not effective by altering the taste of the water passing through the filter medium. Alternatively, the indicator may denote when the filter medium is not effective by altering the color of the water passing through the filter medium. For example, the indicator may impart a color to the water passing through the filter medium.

8 Claims, No Drawings

METHOD OF USING INDICATOR MEANS FOR LIQUID PURIFICATION FILTER

BACKGROUND OF THE INVENTION

The present invention relates to a liquid purification filter, such as a filter for the purification of water.

In the more industrialized countries, such as the United States and western European nations, domestic water supplies generally are regarded as being safe, i.e., as lacking pathogens and/or other agents which may adversely the affect the health of those consuming the water. However, a significant market has developed in these countries for filter systems which provide an additional margin of safety and/or remove materials, such as chlorine, which affect the taste of the water. Such systems include those which are designed to continuously purify all of the water entering a house and smaller filters which may be attached to a single faucet. Still smaller filters are available, such as the Brita® filters which are integrated into a pitcher, for purifying small quantities of water in a batch process.

In countries or communities where the drinking water is not safe, however, reliable filter systems are becoming a necessity. For example, population growth, industrialization, and natural disasters all can contribute to polluted drinking water, even in communities which generally have good sewage disposal and water purification systems in place.

The useful life of most filter systems, regardless of size, typically is based on the volume of water which may be purified by a given system, based either on known or estimated types and amounts of impurities to be removed. Moreover, the volume of water passed through any given filter system often is simply estimated. The filter is replaced after the passage of a predetermined period of time, even though it is not known if the useful life of the filter has been exceeded or even fully utilized.

Finally, defects in a filter can result in the passage of contaminants through the filter system. These defects include channeling in the filter medium, improper sealing, and areas that lack complete treatment, i.e., defects in the filtration medium per se. It is often difficult to determine if any of these defects occur with a particular filter and, therefore, potentially contaminated water is consumed.

Accordingly, there is a need for a means of determining when the useful life of a filter system has been reached, through either failure or overuse.

SUMMARY OF THE INVENTION

The present invention addresses some of the difficulties and problems discussed above by providing a method of indicating the presence of defects which allow contaminants to pass through the filter and, in another permutation, indicating when the useful life of a filter medium has ended. Thus, the indicator means denotes when the filter medium no longer is effective in removing the target substance from the liquid. Accordingly, the present invention provides a method of monitoring the removal by a filter medium of a target substance from a liquid passing through the filter medium. The method involves:

providing an indicator means;

providing a filter medium having a plurality of binding sites which have a first affinity for the target substance and a second affinity for the indicator means;

introducing the indicator means into the liquid;

passing the liquid through the filter medium; and determining the presence or absence of the indicator means in the liquid which has passed through the filter medium.

The first and second affinities are adapted to require binding of the indicator means by the filter medium only so long as binding sites are available to the target substance. Thus, the indicator means is adapted to compete with the target substance. As a practical matter, the liquid typically will be water.

The present invention also provides a method of monitoring the removal by a filter medium of a target substance from a liquid passing through the filter medium. The method involves:

providing a filter medium having a plurality of binding sites which have a first affinity for the target substance and a second affinity for the indicator means;

providing an indicator means in an amount sufficient to occupy a majority of the binding sites of the filter medium;

locating the indicator means at the majority of binding sites of the filter medium;

passing the liquid through the filter medium; and determining the presence or absence of the indicator means in the liquid which has passed through the filter medium.

The indicator means may denote when the filter medium is not effective by altering the taste of the water passing through the filter medium. Alternatively, the indicator means may denote when the filter medium is not effective by altering the color of the water passing through the filter medium. For example, the indicator means may impart a color to the water passing through the filter medium.

DETAILED DESCRIPTION OF THE INVENTION

As used herein, the term "filter medium" is meant to include any material in any form which is capable of selectively removing one or more substances from a liquid. The filter medium may remove such substances by adsorption, inclusion, electrostatic or ionic attraction, or any other means known to those having ordinary skill in the art. The filter medium typically will be porous and granular or particulate in form or in the form of a woven or nonwoven web or a membrane. The term "binding site" in reference to the filter medium is used to generally refer to a region or specific location on or in the filter medium where a target substance may be adsorbed, included or bound. The term is not intended to refer to, or even imply, a particular mechanism for the removal of a target substance from a liquid by a filter medium.

The term "filter system" is used herein to mean the filter medium and associated hardware, such as a housing or container for the filter medium and pipes or tubing for directing a liquid into and out of the housing. The filter system may include a separate housing or container for the indicator means, as well as any other hardware which is either desirable or necessary for a particular application.

As used herein, the term "target substance" is meant to include any substance which is desired to be removed from a liquid. Examples of target substances include, by way of illustration only, heavy metal ions, chlorine and other halogens, bacteria, viruses, protozoa, and the like.

The term "liquid" is used herein to mean any material which normally is a liquid at ambient temperature and pressure, i.e., at about 20°–25° C. and 760 mm Hg. As a practical matter, the liquid of greatest interest is water. However, other liquids may be employed in the method of the present invention, such as alcohols; aliphatic, cycloaliphatic, and aromatic hydrocarbons; halogenated aliphatic and aromatic hydrocarbons; ethers; esters; ketones; aldehydes; and miscellaneous polar solvents such as N,N-dimethylformamide, N-methyl-2-pyrrolidone, tetrahydrofuran, and 1,4-dioxane.

As used herein, the term "indicator means" is meant to include any means for indicating when the filter medium no longer is effective in removing the target substance from the liquid.

As stated earlier, the present invention provides a method of monitoring the removal by a filter medium of a target substance from a liquid passing through the filter medium. The method involves providing an indicator means and a filter medium. The filter medium will have a plurality of binding sites which have a first affinity for the target substance and a second affinity for the indicator means. The first and second affinities are adapted to require binding of the indicator means by the filter medium only so long as binding sites are available to the target substance.

The term "available" is used herein to mean that there are present in the filter medium binding sites which are not occupied by either the target substance or the indicator means (referred to hereinafter as unoccupied binding sites), and that such unoccupied binding sites may be contacted by the liquid passing through the filter medium. By way of illustration, a portion of a filter medium may have a large number of unoccupied binding sites which cannot be contacted by the liquid because of channeling and, therefore, are not available.

In carrying out the method, the indicator means is introduced into the liquid before it passes through the filter medium (i.e., upstream from the filter medium) and the liquid is passed through the filter medium. The presence or absence of the indicator means in the liquid which has passed through the filter medium (i.e., downstream from the filter medium) then is determined.

The indication of defects in, or exceeding the capacity of, the filter medium is based on the ability of the indicator means to interact with the filter medium in a manner analogous to that of the target substance. Thus, when a defect or over-capacity allows the target substance to pass through the filter medium, the indicator means also will pass through the filter medium. It is the detection of the indicator means which produces the indication of the defect or over-capacity. This detection may be based on a change in taste or color of the liquid or some other indication.

The indicator means may be included in the filter medium when the first and second binding affinities are such that the indicator means will not be displaced by the target substance unless and until unoccupied binding sites no longer are available in the filter medium. There is the possibility, however, that this arrangement may not permit release of the indicator means into the liquid passing through the filter medium because of channeling or some other defect.

Alternatively, and desirably, the indicator means may be located upstream from the filter medium, either in a separate housing or in the same housing as the filter medium. The indicator means may be released into the liquid upstream from the filter medium continuously, intermittently by a timed-release mechanism, or manually.

The indicator means may be one with a bitter or otherwise negative or recognizable taste. When a threshold quantity of the substance is present in the liquid, it would be tasted and alert the user of filter failure or over-capacity. Bitter compounds include caffeine, nicotine, urea, quinine, brucine, Bitrex® (B. I. Chemicals Inc.; Montvale, N.J.), among others. These compounds themselves may function as the indicator means or they may be conjugated to a carrier molecule which interacts with the filter in a manner analogous to that of the target substance. For example, a filter medium which is based on electrostatic or ionic interaction and adsorbs negatively charged molecules or particles, such as some microorganisms, may utilize an indicator means of caffeine conjugated to sulfated cyclodextrin with approximately the same charge as the target contaminant.

As already noted, the indication of exhaustion of the filter is accomplished through competition of the indicator means with the target substance for sites on the filter medium. The indicator means may have approximately the same affinity for the filter as the target substance or possibly less affinity. The indicator means may occupy filter medium sites and is removed by the target substance when there no longer are any unoccupied sites available to the target substance. Alternatively, the indicator means may be present in a majority of the binding sites of the filter medium and the indicator means is removed by the target substance as binds to the filter medium. The exhaustion of the indicator means indicates exhaustion of the filter medium. In this case, the indicator means may have a pleasant taste which would last throughout the lifetime of the filter medium.

A particularly useful filter medium is the charge-modified nonwoven filter described in U.S. patent application Ser. No. 08/594,879, filed Feb. 7, 1996 in the names of Dennis S. Everhart et al., which application is incorporated herein in its entirety. Such filter is useful for removing charged, micron to sub-micron sized particles from an aqueous liquid. The filter is composed of: (1) a filter sheet having a plurality of individual exposed surfaces, at least a portion of which have a surface energy of less than about 45 dynes per centimeter; (2) amphiphilic macromolecules adsorbed onto at least some individual exposed surfaces having a surface energy of less than about 45 dynes per centimeter; and (3) chemical charge modifiers incorporated onto at least a portion of the amphiphilic macromolecules; so that when the charge-modified filter is in contact with the aqueous liquid containing the charged, micron to sub-micron sized particles, the particles are adsorbed onto the chemically charge-modified filter.

In general, the amphiphilic macromolecules adsorbed on the filter sheet have both hydrophobic regions and hydrophilic regions. Useful amphiphilic macromolecules include, but are not limited to, amphiphilic proteins. The amphiphilic proteins may be selected from classes of globular and/or random coil proteins. For example, the amphiphilic proteins may be milk proteins. Desirably, the amphiphilic proteins may include proteins such as those found in bovine milk, including, for example, various caseins and whey proteins.

The chemical charge modifiers that are incorporated onto the amphiphilic macromolecule coating may be chemical charge modifiers including, but not limited to, polyvalent cations, cationic polymers, and positively-charged particles. As an example, the chemical charge modifiers may be polyvalent cations including, but not limited to, $Ca^{2+}$, $Al^{3+}$, and $Bi^{3+}$. The chemical charge modifiers also may be positively charged particles such as, for example, single metal hydroxides, mixed metal hydroxides, and sol-gels. Exemplary positively charged particles include $AlO(OH)$, $Bi(OH)_3$, and codepositions of $Fe(OH)_3$ and $Mg(OH)_2$.

The chemical charge modifiers also may be cationic polymers such as, for example, quaternary amine-containing cationic resins, aliphatic amines having at least one primary and/or secondary amine, and the like. The chemical charge modifiers may be cationic polymer systems composed of a primary polymer material and a secondary polymer material. For example, the cationic polymer system may be composed of a primary polymer material such as polyamine epichlorohydrin and a secondary polymer material such as tetraethylene pentamine.

The filter sheet may be a matrix of fibrous material. Suitable matrices of fibrous material may be, for example, woven fabrics, knit fabrics, and nonwoven fabrics. The matrix of fibrous material may be a nonwoven fabric such as, for example, a nonwoven web of meltblown fibers, a nonwoven web of continuous spunbond filaments, and a bonded carded web. by way of example, a nonwoven of meltblown fibers may further include one or more secondary materials selected from the group consisting of textile fibers, wood pulp fibers, particulate materials, and superabsorbent materials. The fibrous material may be formed from a thermoplastic polymer. For example, the thermoplastic polymer may be selected from polyethylene, polypropylene, polybutene, ethylene copolymers, propylene copolymers, and butene copolymers and blends of the same.

If desired, at least a portion of the fibrous material may be a multicomponent material or a bicomponent material selected from multicomponent and bicomponent fibers and filaments. At least a portion, if not all, of these fibers may be textured by use of an expanding agent.

The filter sheet also may be a permeable sheet such as a membrane filter or an apertured, film-like material. The apertured, film-like material may include, but is not limited to, perf-embossed films, one or more textured apertured films, reticulated apertured films, contoured apertured films, film-nonwoven apertured laminates, expanded plexifilamentary films, and combinations of the same. The apertured film-like material may further include one or more secondary materials.

The apertured film-like material may be formed from a thermoplastic polymer. For example, the thermoplastic polymer may be selected from polyolefins, polyamides, and polyesters. If the polymer is a polyolefin, it may be selected from polyethylene, polypropylene, polybutene, ethylene copolymers, propylene copolymers, and butene copolymers and blends of the same. The permeable sheet may be composed of combinations of one or more matrices of fibrous material and apertured film-like material.

The chemically charged-modified filter may have a basis weight of from about 6 to about 400 grams per square meter (gsm). For example, the filter may have a basis weight of from about 12 to about 250 gsm. As a further example, the filter may have a basis weight of from about 17 to about 102 gsm.

The chemically charged-modified filter may be a multilayer filter material including at least two layers of the chemically charge-modified filter described above. The multilayer material also may include at least one layer of the chemically charge-modified filter described above and at least one other layer. The other layer may be selected from woven fabrics, knit fabrics, bonded carded webs, continuous spunbond filament webs, meltblown fiber webs, films, apertured films, and combinations thereof. Finally, the chemically charge-modified filter may be configured into a shape such as, for example, a tube, cylinder, cone, cube, sphere, or the like.

The present invention is further described by the examples which follow. Such examples, however, are not to be construed as limiting in any way either the spirit or the scope of the present invention.

EXAMPLE 1

This example illustrates the removal of colored microparticles by a charge-modified filter.

Royal blue dyed, carboxylated polystyrene particles having an average diameter of 0.3 micrometer were obtained from Bangs Laboratories (Carmel, Ind.). A test liquid was prepared by diluting 1 part of the carboxylated polystyrene microparticles with 5,000 parts of distilled, deionized water which resulted in approximately $1.5 \times 10^9$ particles/ml of test liquid. A polypropylene meltblown nonwoven web having a basis weight of 1.0 ounce per square yard or osy (about 34 grams per square meter or gsm) was charge-modified with a nonfat milk coating (Carnation®, Nestle Food Company, Glendale, Calif.) under shear as described in U.S. Pat. No. 5,494,744 to Everhart et al. (incorporated herein by reference in its entirety) and rinsed with a copious amount of water. A second coating of a quaternary ammonium compound, Reten® 201 (Hercules Inc., Wilmington, Del.) was applied with shear to provide a cationic surface. These filters have been demonstrated to remove 99% of cholera from water (see application Ser. No. 08/594,879, supra).

A Coulter® Model N4MD submicron particle analyzer (Coulter Corporation, Miami, Fla.) was used to measure the number of particles in the liquid. A standard curve based on known concentrations of microparticles and counts/second measurements on the N4MD was developed. Two, 25-mm diameter disks of the charge-modified filters were placed in a stainless steel filter apparatus, a microsyringe having a 25-mm luer inlet (Catalog No. 3002500, Millipore Corporation, Bedford, Mass.). Four ml of test liquid was forced through the filters using a syringe at an approximate rate of 0.1 ml/sec. The liquid was collected in a quartz cuvette and measured in the N4MD at a 90° detector angle. The charge-modified filters removed 61% of the microparticles and the filters appeared blue. Untreated meltblown nonwoven web having the same basis weight was tested in the same way as a control; no removal of microparticles was detected. The data are summarized in Table 1.

TABLE 1

| Summary of Microparticle Removal | | | |
|---|---|---|---|
| Filter | Counts/second | Particles removed | % Reduction |
| Control web | $7.7 \times 10^5$ | 0 | 0 |
| Charge-modified filter | $5.0 \times 10^5$ | $9.2 \times 10^8$ | 61 |

The charged-modified filter carried a positive charge which resulted from the quaternary ammonium compound on the surfaces of the fibers of which the web was composed. Thus, the filter was designed to remove oppositely charged, i.e., negatively charged, particles from a fluid stream. The carboxylated polystyrene particles were negatively charged and, therefore, would compete with a similarly charged substance intended to be removed by the filter medium.

EXAMPLE 2

This example illustrates the removal of caffeinated, phosphorlyated cyclodextrin by a charge-modified filter.

Cavitron™ phosphorlyated beta-cyclodextrin/caffeine complex was obtained from American Maize Products Company (Hammond, Ind.). A test liquid was prepared by dissolving 1.5 g of the cyclodextrin complex in 70 ml of distilled, deionized water. The initially neutral pH was adjusted to approximately pH 10 with sodium hydroxide solution. The charge-modified nonwoven web described in Example 1 was employed.

The Coulter® Model N4MD submicron particle analyzer described in Example 1 was used to measure the number of particles in the liquid. Three 25-mm diameter disks of the charge-modified filters were placed in a stainless steel filter apparatus. Four ml of liquid was forced through the filters using a syringe at an approximate rate of 0.1 ml/sec. The liquid was collected in a quartz cuvette and measured in the N4MD at a 62.6° detector angle. Charge-modified filters removed a significant amount of the cyclodextrin when the pH was basic, but not when the pH was neutral. Untreated meltblown material was tested in the same way as a control and no removal of microparticles was detected. The results are summarized in Table 2.

TABLE 2

Summary of Microparticle Removal

| Filter | pH | Counts/second |
|---|---|---|
| None | 7 | $5.2 \times 10^5$ |
| Control web | 7 | $4.1 \times 10^5$ |
| Charge-modified filter | 7 | $3.8 \times 10^5$ |
| None | 10 | $5.1 \times 10^5$ |
| Control web | 10 | $5.4 \times 10^5$ |
| Charge-modified filter | 10 | $3.5 \times 10^5$ |

As with Example 1, the particles were negatively charged and would compete with a similarly charged substance intended to be removed by the filter medium.

While the specification has been described in detail with respect to specific embodiments thereof, it will be appreciated by those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of monitoring the removal by a filter medium of a target substance from a liquid passing through the filter medium, the method comprising:

providing an indicator means;

providing a filter medium having a plurality of binding sites which have a first affinity for the target substance and a second affinity for the indicator means;

introducing the indicator means into the liquid;

passing the liquid through the filter medium; and determining the presence or absence of the indicator means in the liquid which has passed through the filter medium;

wherein the first and second affinities are adapted to require binding of the indicator means by the filter medium only so long as binding sites are available to the target substance.

2. The method of claim 1, in which the liquid is water.

3. The method of claim 2, in which the indicator means alters the taste of the water.

4. The method of claim 2, in which the indicator means alters the color of the water.

5. A method of monitoring the removal by a filter medium of a target substance from a liquid passing through the filter medium, the method comprising:

providing a filter medium having a plurality of binding sites which have a first affinity for the target substance and a second affinity for the indicator means;

providing an indicator means in an amount sufficient to occupy a majority of the binding sites of the filter medium;

locating the indicator means at the majority of binding sites of the filter medium;

passing the liquid through the filter medium; and determining the presence or absence of the indicator means in the liquid which has passed through the filter medium;

wherein the first and second affinities are adapted to require release of the indicator means from the filter medium when filter medium binding sites no longer are available to the target substance.

6. The method of claim 5, in which the liquid is water.

7. The method of claim 6, in which the indicator means alters the taste of the water.

8. The method of claim 6, in which the indicator means alters the color of the water.

* * * * *